United States Patent [19]
Fischer

[11] Patent Number: 5,403,310
[45] Date of Patent: Apr. 4, 1995

[54] INSTRUMENT FOR ELECTRO-SURGICAL EXCISOR FOR THE TRANSFORMATION ZONE OF THE UTERINE CERVIX AND METHOD OF USING SAME

[76] Inventor: Nathan R. Fischer, 17 Lovelace Dr., West Hartford, Conn. 06117

[21] Appl. No.: 192,132

[22] Filed: Feb. 4, 1994

[51] Int. Cl.6 .......................................... A61B 17/39
[52] U.S. Cl. ........................................ 606/45; 606/49
[58] Field of Search ................... 606/32, 33, 37, 39, 606/40, 41, 45, 46, 47, 49, 119, 170; 128/122, 639, 642, 649

[56] References Cited
U.S. PATENT DOCUMENTS

| | | |
|---|---|---|
| 1,741,740 | 12/1929 | Sederholm et al. |
| 2,447,169 | 8/1948 | De Sousa |
| 4,485,812 | 12/1984 | Harada et al. |
| 4,834,095 | 5/1989 | Miller |
| 4,846,175 | 7/1989 | Frimberger |
| 4,887,593 | 12/1989 | Wiley et al. |
| 4,924,882 | 5/1990 | Donovan |
| 5,133,713 | 7/1992 | Huang et al. |

*Primary Examiner*—Lee S. Cohen
*Assistant Examiner*—Stephen Huang

[57] ABSTRACT

An electro-surgical instrument for excision of a tissue specimen from the transformation zone of the uterine cervix includes an elongated body member with an endocervical portion at one end, a contact portion at the other end, and a vaginal portion therebetween. A stop arm extends at a right angle to the body member at the juncture of the endocervical and vaginal portions, and a wire electrode extends diagonally between the stop arm and endocervical portion. In using the instrument, the endocervical portion is inserted through the vaginal canal and into the endocervical canal of the uterine cervix until the electrode contacts an area of the ectocervix without colposcopically evident pathology. Current is imparted to the electrode and the instrument is advanced into the endocervical canal until the stop arm abuts the ectocervix, after which the instrument is rotated one full revolution to cut a conically shaped tissue specimen from the transformation zone of the uterine cervix which is withdrawn with the instrument.

18 Claims, 3 Drawing Sheets

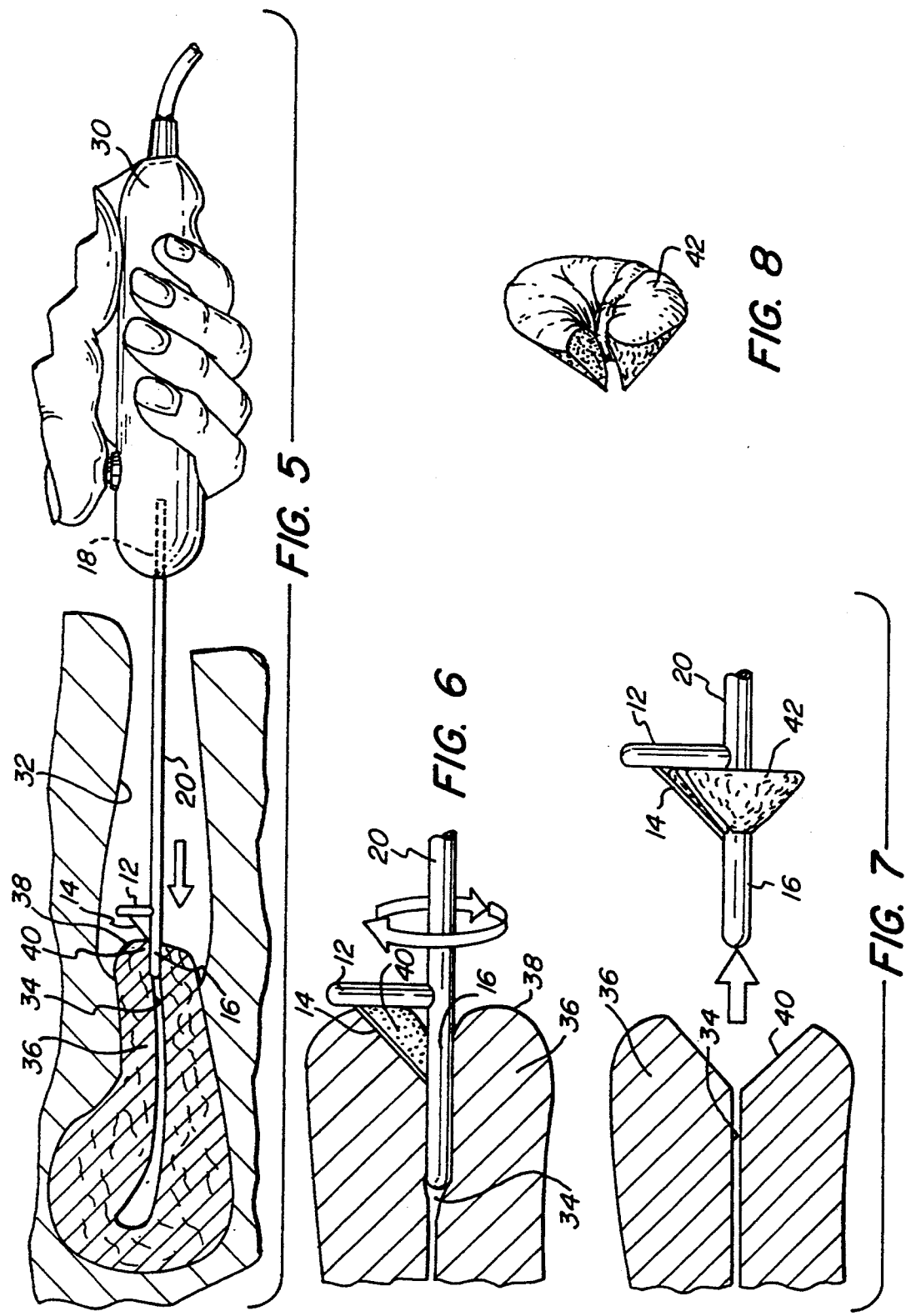

5,403,310

1

INSTRUMENT FOR ELECTRO-SURGICAL EXCISOR FOR THE TRANSFORMATION ZONE OF THE UTERINE CERVIX AND METHOD OF USING SAME

BACKGROUND OF THE INVENTION

The present invention relates to an electro-surgical excisor, and more particularly, to an electro-surgical excisor used for excising a tissue specimen from the transformation zone of the uterine cervix.

Cervical intraepithelial neoplasia has been on the increase in recent years, but successful ablation treatment has been provided by procedures such as electrocoagulation, electrodiathermy, cryosurgery, and laser surgery. With such procedures, it is important for the physician to recognize and biopsy invasive cancers to avoid their unintentional ablation.

Recently, biopsy specimens of this type of lesion has been successfully obtained by use of wire loop electrodes. Such electrodes allow the lesions and the transformation zone to be removed in their entirety and made available for a pathological analysis.

In using a loop electrode on the end of a handle, there is typically no guiding support during the excision. As a result, there is a risk of injury to the surrounding tissue which would result in a longer recovery period for the patient. Further, the amount of tissue obtained may vary in amount and definition, leading to difficulties in the pathological analysis.

It is an object of the present invention to provide a novel electro-surgical excisor which permits the complete severance of a controlled tissue specimen in a single revolution of the excisor.

It is also an object to provide such an electro-surgical excisor which minimizes the potential for injury to adjacent healthy tissue.

It is a further object to provide such an electro-surgical excisor which obtains a more defined and controlled amount of cervical tissue, making excision of the lesion and pathological interpretation easier.

SUMMARY OF THE INVENTION

It has now been found that the foregoing and related objects may be readily attained in an electro-surgical instrument for excision of a tissue specimen from the transformation zone of the uterine cervix, and it includes an elongated body member having an endocervical portion at one end, a contact portion at the other end, and a vaginal portion therebetween. The endocervical portion is insertable into and rotatable in the uterine cervix. A stop arm extends substantially at a right angle to the body member at the juncture of the endocervical portion and the vaginal portion, and a wire electrode extends diagonally from the stop arm to the endocervical portion. The elongated body member is dimensioned to extend outwardly of the vaginal canal when the endocervical portion is inserted into the uterine cervix to allow the instrument to be manipulated externally of the vaginal canal. Generally, the endocervical portion is about 12-22 mm in length, and a unidirectional stop arm is about 9-11 mm in length, and each bidirectional stop arm is about 7.5-10 mm. The stop arm may extend in only one direction or in both directions from the body member.

The electrode is fastened to the endocervical portion at a point spaced inwardly from its free end, usually about 10-14 mm, and to the stop arm at a point spaced inwardly from its free end, generally about 1-3 mm for a bidirectional stop arm and 3-5 mm for a unidirectional stop arm.

In excising a specimen from the transformation zone of the uterine cervix, the endocervical portion of the instrument is inserted through the vaginal canal and into the endocervical canal of the uterine cervix until the electrode contacts an area of the ectocervix without colposcopically evident pathology. Current is supplied to the electrode and the instrument is advanced into the endocervical canal until the stop arm abuts the ectocervix. This cuts into the transformation zone of the uterine cervix, after which the instrument is rotated one full revolution about its axis with the stop arm abutting the ectocervix to cut a conically shaped tissue specimen from the transformation zone of the uterine cervix. The current to the electrode is discontinued, and the instrument and the specimen are withdrawn from the vaginal canal.

Preferably, the current is of a value to effect both cutting and coagulation, generally to produce power in the range of 50–70 watts. The body portion of the electrode is dimensioned so that the insertion results in the body member extending outwardly of the vaginal canal with the endocervical portion in the uterine cervix; in this manner, the instrument is manipulated externally of the vaginal canal.

Usually, the current to the electrode is discontinued after the advancing step and before the rotating step to allow for preparation for the rotation step. Thereafter, the current is again supplied to the electrode prior to the rotating step.

BRIEF DESCRIPTION OF THE DRAWINGS

FIG. 5 is a diagrammatic view of the electro-surgical excisor being inserted into the vaginal canal and uterine cervix, and showing the excisor mounted in the manipulator of an electro-surgical unit;

FIG. 6 is a diagrammatic side view of the fragment only illustrated electro-surgical excisor seated in the endocervical canal with arrows showing rotation of the excisor for tissue excision;

FIG. 7 is a diagrammatic view similar to FIG. 6 after the excisor and excised tissue specimen have been withdrawn;

FIG. 8 is a perspective view of the tissue specimen after removal from the electro-surgical excisor;

DETAILED DESCRIPTION OF THE PREFERRED EMBODIMENT

Figure 1:
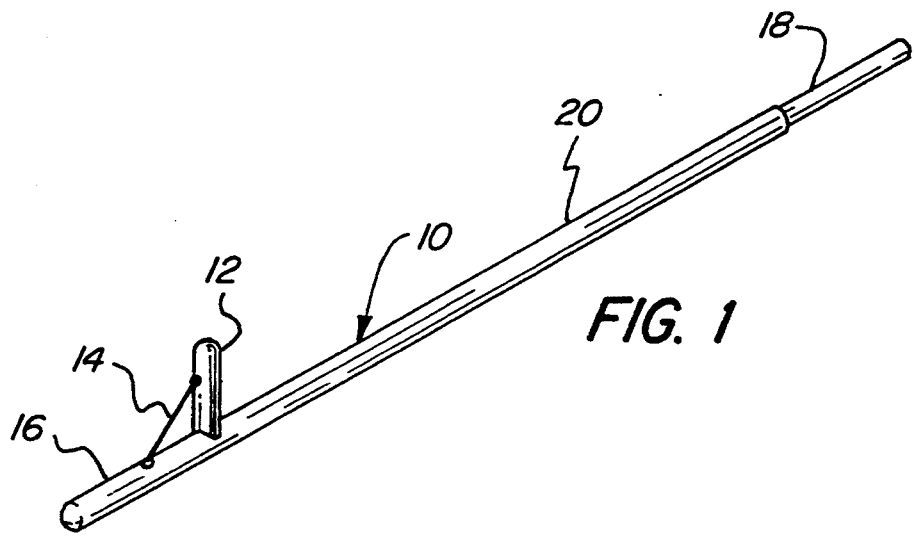
FIG. 1 is a perspective view of an electro-surgical excisor embodying the present invention.

Turning first to FIGS. 1-4, an electro-surgical excisor embodying the present invention is illustrated therein as having an elongated body member generally designated by the numeral 10, a stop arm 12, and an electrode 14. The body member 10 has an endocervical portion 16 at one end thereof, a contact portion 18 at its other end, and a vaginal portion 20 therebetween.

The stop arm 12 extends at a right angle to the body member 10, intersecting it at the juncture of the endocervical portion 16 and the vaginal portion 20. The electrode 14 is formed from a thin wire and extends diagonally from the stop arm 12 to the endocervical portion 16.

Figure 3:
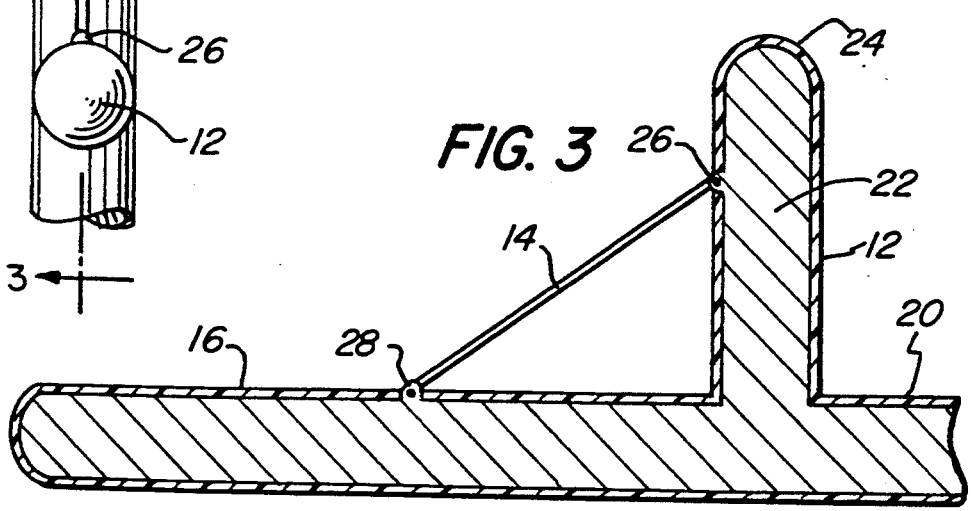
FIG. 3 is a sectional view along the line 3–3 of FIG. 2 drawn to a still enlarged scale.

As best seen in FIG. 3, the body member 10 and stop arm 12 have an integrally formed core 22 formed of an electroconductive material such as stainless steel. This core 22 is covered with a coating 24 of electrically insulating material such as polytetrafluoroethylene, or other insulating synthetic resin, except over the contact portion 18.

The stop arm 12 has an anchor bead 26 of electrically conductive material which is in electrical contact with the core 22 and spaced inwardly from the free end of the stop arm 12. Similarly, spaced inwardly from the free end of the endocervical portion 16 is a bead 28 which is in electrical contact with the core 22. The electrode 14 is bonded to the beads 26, 28, and thereby makes electrical contact with the core 22.

Figure 4:
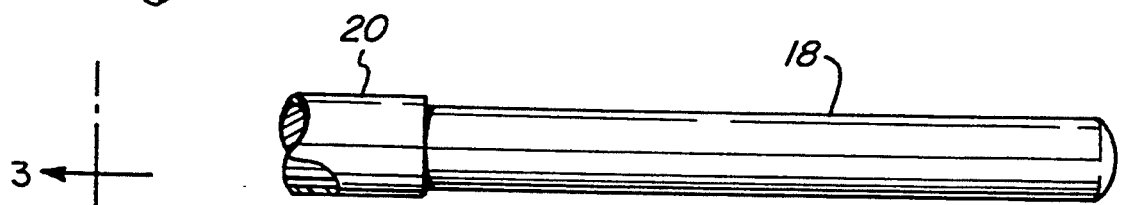
FIG. 4 is a fragmentary side view of the contact end portion of the electro-surgical excisor.
Figure 2:
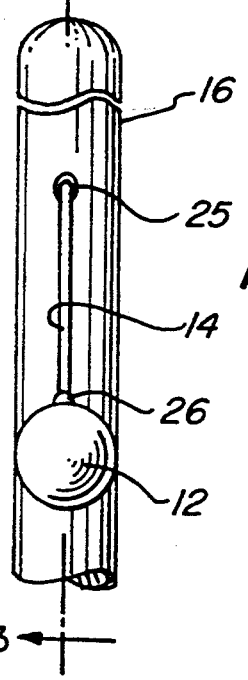
FIG. 2 is a fragmentary plan view of the electrode end portion thereof showing the stop arm, electrode, and endocervical portion, drawn to a scale enlarged from that of FIG. 1.

Referring to FIG. 4, the uncoated contact portion 18 is dimensioned to fit a manipulator 30, as shown in FIG. 5, of a standard electro-surgical unit (not shown) so that current will flow therethrough to the electrode 14.

As best seen in FIG. 5, the body member 10 of the electrosurgical excisor is dimensioned so that the contact portion 18 is disposed outwardly of the vaginal canal 32 when the endocervical portion 16 is inserted into the endocervical canal 34 of the uterine cervix 36.

In a working embodiment, the elongated body member 10 is about 120-140, and preferably 130, mm in length, with an endocervical portion 16 of about 18-22, and preferably 20 mm, a vaginal portion 20 of about 80-100, and preferably 90 mm, and a contact portion 18 of about 8-12, and preferably 20 mm. The stop arm 12 is about 8-12. and preferably 10 mm in length. The anchor bead 26 is positioned on the stop arm 12 about 3-5, and preferably, 4 mm from its free end, and the anchor bead 28 is positioned on the endocervical portion 16 approximately 12 mm from its free end.

The use of the electro-surgical excisor is shown in FIGS. 5-8. Referring first to FIG. 5, the endocervical portion 16 of the excisor is inserted through the vaginal canal 32 and into the endocervical canal 34 of the uterine cervix 36 until the electrode 14 contacts an area of the ectocervix 38 which is free from colposcopically evident pathology. Through use of the manipulator 30, current is imparted to the electrode 14, and the endocervical portion 16 is advanced in the direction shown by the arrow in FIG. 5 into the endocervical canal 34 until the stop arm 12 abuts the ectocervix 38 as shown in FIG. 6. In this manner, a cut is made in the transformation zone 40 of the uterine cervix 36 by the electrode 14.

At this point, current to the electrode 14 may be discontinued to permit preparation for the next step. Once preparation is completed, current is again imparted to the electrode 14 and the excisor is rotated one full revolution along its axis, as shown by the arrows in FIG. 6. Because rotation takes place with the endocervical portion 16 in the endocervical canal 34, and with the stop arm 12 abutting the ectocervix 38, the excisor is stabilized, allowing for a conically shaped tissue specimen 42 to be excised from the transformation zone 40 of the uterine cervix 36.

Once the excision is complete, current is discontinued to the electrode 14 and the excisor is withdrawn from the endocervical canal 34 and the vaginal canal 32, withdrawing the tissue specimen 42 with it. As shown in FIG. 8, the tissue specimen 42 will be conical in shape providing a defined and controlled amount of cervical tissue to make pathological interpretation easier and more reliable. The current employed for the excision process is one appropriate for cutting and coagulation and will typically provide an output power in the range of 50-70 watts.

Figure 9:
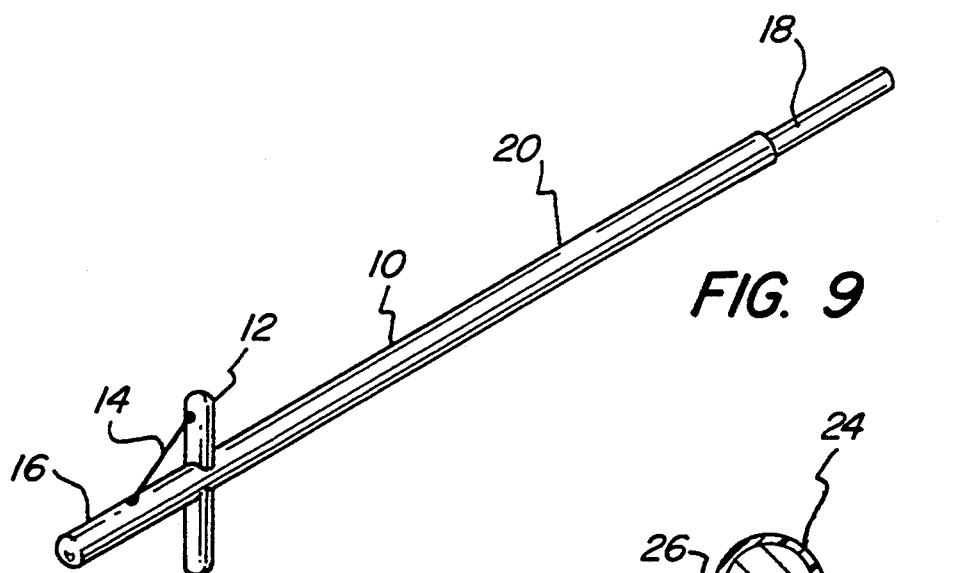
FIG. 9 is a perspective view of an alternate embodiment of the invention in which the stop arm extends in both directions from the body.
Figure 10:
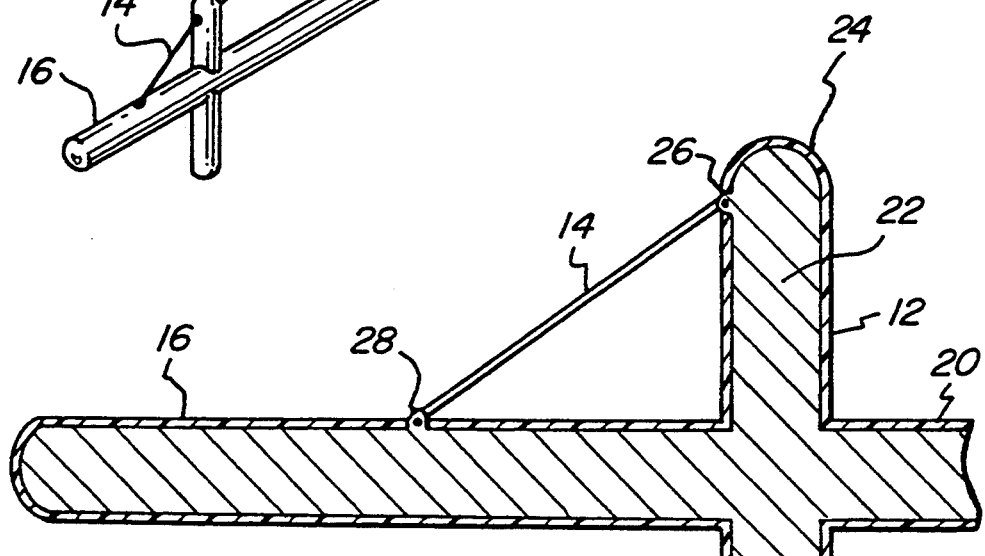
FIG. 10 is a fragmentary sectional view of the embodiment of FIG. 9 drawn to an enlarged scale.
Figure 11:
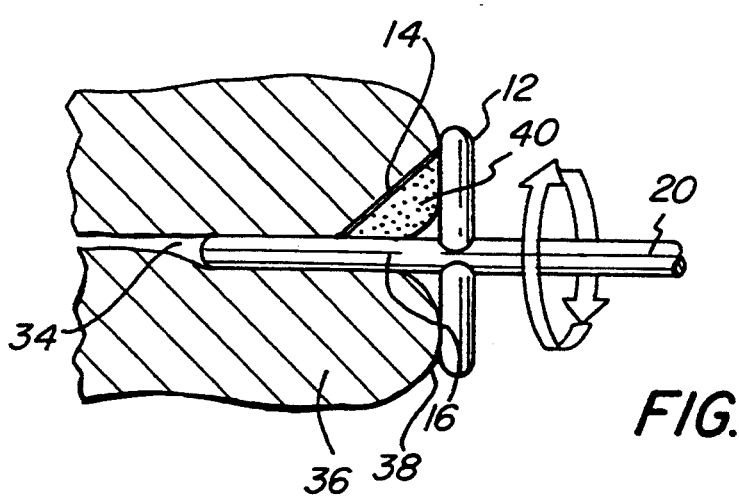
FIG. 11 is a view similar to FIG. 6 showing the manner in which the elements of the bidirectional stop arm seat about the cervix to increase stability.

In FIGS. 9 and 10, there is shown an activated embodiment of the invention in which the stop arm 12 has two portions which extend in opposite directions (i.e., 180° apart) from the body member 10. This increases the surface of the cervix against which the instrument will bear while allowing a reduction in the length of the arm if it were to project in only one direction. In this embodiment, each projecting length will normally be 7.5-10 mm and the electrode may be spaced closer to the free end, i.e., about 1-2 mm. FIG. 11 illustrates the manner in which the bidirectional stop arm seats on opposite sides of the cervical canal to increase stability during rotation.

Electro-surgical excisors having the electrode positioned at varying angles, as appropriate for different clinical situations, may be fabricated by altering the position of anchor bead 26 on stop arm 12 and/or the position of anchor bead 28 on endocervical portion 16.

Thus, it can be seen from the foregoing detailed specification and attached drawings that the novel electro-surgical excisor of the present invention enables complete severance of the cervical tissue in a single revolution of the excisor while preventing injury to the adjacent healthy tissue. Additionally, use of the excisor enables the excisor of a defined and controlled amount of cervical tissue, making excision of the lesion and pathological interpretation easier. No special equipment is necessary for the excisor of the present invention which may be utilized in existing electro-surgical apparatus.

What is claimed is:

1. An electro-surgical instrument for excision of a tissue specimen from a transformation zone of a uterine cervix by insertion through a vaginal canal comprising:
   (a) an elongated body member having two ends with an endocervical portion adjacent one end, a contact portion adjacent the other end, and a vaginal portion therebetween, said endocervical portion being insertable into and rotatable in the uterine cervix;
   (b) a stop arm extending substantially at a right angle to said body member at a juncture of said endocervical portion and said vaginal portion; and
   (c) a wire electrode extending diagonally from said stop arm to said endocervical portion.

2. The electro-surgical instrument in accordance with claim 1 wherein said stop arm has portions extending in both directions from said body member at 180° from each other.

3. The electro-surgical instrument in accordance with claim 2 wherein said endocervical portion is about 12-22 mm in length and each element of said bidirectional stop arm is about 7.5-10mm in length.

4. The electro-surgical instrument in accordance with claim 1 wherein said elongated body member is dimensioned to extend outwardly of a vaginal canal when the endocervical portion is inserted into the uterine cervix to allow said instrument to be manipulated externally of the vaginal canal.

5. The electro-surgical instrument in accordance with claim 1 wherein said electrode is fastened to said endocervical portion at a point spaced inwardly from said one of said body member.

6. The electro-surgical instrument in accordance with claim 5 wherein said endocervical portion is about 20 mm in length.

7. The electro-surgical instrument in accordance with claim 5 wherein said electrode is fastened to said stop arm at a point spaced inwardly from its end spaced from said body member.

8. The electro-surgical instrument in accordance with claim 7 wherein said stop arm is unidirectional and about 9-11 mm in length.

9. The electro-surgical instrument in accordance with claim 7 wherein said stop arm has portions extending from said body member at 180° to each other and each portion thereof is about 7.5-10mm in length and said electrode is fastened to one of said portions of said stop arm at a point about 1-3 mm from its end spaced from said body member.

10. An electro-surgical instrument for excision of a tissue specimen from a transformation zone of a uterine cervix by insertion through a vaginal canal comprising:
   (a) an elongated body member having two ends with an endocervical portion adjacent one end, a contact portion adjacent the other end, and a vaginal portion therebetween, said endocervical portion being insertable into and rotatable in the uterine cervix, said elongated body member being dimensioned to extend outwardly of the vaginal canal when said endocervical portion is inserted into the uterine cervix to allow said instrument to be manipulated externally of the vaginal canal;
   (b) a stop arm extending substantially at a right angle to said body member at a juncture of said endocervical portion and said vaginal portion; and
   (c) a wire electrode extending diagonally from a point spaced inwardly from an end of said stop arm spaced from said endocervical portion at said body member to a point spaced inwardly from said one end of said body member.

11. The electro-surgical instrument in accordance with claim 10 wherein said endocervical portion is about 12-22 mm in length with said electrode being fastened thereto at a point about 10-14 mm from said one end of said body member.

12. The electro-surgical instrument in accordance with claim 11 wherein said stop arm is unidirectional and about 9-11 mm in length and said electrode is fastened thereto at a point inwardly of its end spaced from said body member.

13. The electro-surgical instrument in accordance with claim 11 wherein said stop arm has portions extending from said body member at 180° to each other and each portion is about 7.5-10 mm in length and wherein said electrode is fastened to one of said portions at a point about 1-3 mm from its end spaced from said body member.

14. A method for excising a specimen from the transformation zone of a uterine cervix of a patient by insertion through a vaginal canal comprising the steps of:
   (a) providing an electro-surgical instrument comprising an elongated body member having two ends with an endocervical portion adjacent one end, a contact portion adjacent the other end, and a vaginal portion therebetween, a stop arm extending substantially at a right angle to said body member at the juncture of said endocervical portion and said vaginal portion, and a wire electrode extending diagonally from said stop arm to said endocervical portion;
   (b) inserting said endocervical portion of said instrument through the vaginal canal and into the endocervical canal of the uterine cervix of a patient until said electrode contacts an area of the ectocervix without colposcopically evident pathology;
   (c) imparting current to said electrode;
   (d) advancing said instrument into said endocervical canal until said stop arm abuts said ectocervix, thereby cutting into the transformation zone of said uterine cervix with said electrode;
   (e) rotating said instrument one full revolution about its axis with said stop arm abutting said ectocervix to cut a conically shaped tissue specimen from said transformation zone of said uterine cervix;
   (f) discontinuing current to said electrode; and
   (g) withdrawing said instrument and said specimen from the vaginal canal.

15. The method for excising a specimen in accordance with claim 14 wherein the current imparting step involves imparting a current of a value to effect both cutting and coagulation.

16. The method for excising a specimen in accordance with claim 15 wherein said current produces power in the range of 50-70 watts.

17. The method for excising a specimen in accordance with claim 14 wherein said body portion of said electrode is dimensioned so that said inserting step results in said body member extending outwardly of said vaginal canal when said endocervical portion is inserted into said uterine cervix whereby said instrument may be manipulated externally of said vaginal canal.

18. The method for excising a specimen in accordance with claim 14 including the step of discontinuing current to said electrode after the advancing step and before the rotating step to allow for preparation for the rotating step and further including the step of again imparting current to said electrode prior to the rotating step.

* * * * *

UNITED STATES PATENT AND TRADEMARK OFFICE
CERTIFICATE OF CORRECTION

PATENT NO.   :  5,403,310
DATED        :  April 4, 1995
INVENTOR(S)  :  Nathan R. Fischer It is certified that error appears in the above-indentified patent and that said Letters Patent is hereby corrected as shown below:

Column 5, line 3, delete "element" and insert --portion--; same line, delete "bidirectional".

Column 5, line 14, after "one" insert --end--.

Signed and Sealed this

Eighth Day of August, 1995

BRUCE LEHMAN

*Attest:*

*Attesting Officer*            *Commissioner of Patents and Trademarks*